(12) United States Patent
Bloomberg et al.

(10) Patent No.: US 11,529,449 B2
(45) Date of Patent: Dec. 20, 2022

(54) MEDICAL DEVICE DISLODGMENT DETECTION

(71) Applicant: Medtronic, Inc., Minneapolis, MN (US)

(72) Inventors: Daniel Bloomberg, Minneapolis, MN (US); VenKatesh Manda, Stillwater, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 237 days.

(21) Appl. No.: 16/780,988

(22) Filed: Feb. 4, 2020

(65) Prior Publication Data

US 2020/0324038 A1 Oct. 15, 2020

Related U.S. Application Data

(60) Provisional application No. 62/834,051, filed on Apr. 15, 2019.

(51) Int. Cl.
*A61M 1/36* (2006.01)
*A61M 1/16* (2006.01)
*A61M 25/00* (2006.01)

(52) U.S. Cl.
CPC ........ *A61M 1/3656* (2014.02); *A61M 1/1601* (2014.02); *A61M 1/3661* (2014.02);
(Continued)

(58) Field of Classification Search
CPC .............. A61M 1/3656; A61M 1/1601; A61M 1/3661; A61M 1/3655; A61M 2025/0002;
(Continued)

(56) References Cited

U.S. PATENT DOCUMENTS 8,192,388 B2 * 6/2012 Hogard ............... A61M 60/531
604/6.11
8,197,431 B2 * 6/2012 Bennison .......... A61M 5/16836
600/462

(Continued)

FOREIGN PATENT DOCUMENTS

| EP | 2941282 A1 | 11/2015 |
| WO | 9924145 A1 | 5/1999 |
| WO | 2017112517 A1 | 6/2017 |

OTHER PUBLICATIONS

Korkut et al., "Patency and Venous Pressure of Arteriovenous Fistulas for Hemodialysis," Asian cardiovascular thoracic annals, vol. 13, No. 2, Jul. 2005, 5 pp.

(Continued)

*Primary Examiner* — Susan S Su
*Assistant Examiner* — Eric Rassavong
(74) *Attorney, Agent, or Firm* — Shumaker & Sieffert, P.A.

(57) ABSTRACT

In examples described herein, a system includes an elongate member configured to be introduced into vasculature of a patient. The elongate member includes a pressure sensor configured to generate a pressure signal indicative of pressure in the vasculature adjacent the needle. The system includes processing circuitry configured to receive the pressure signal from the pressure sensor, detect, based on the pressure signal, dislodgment of the elongate member from the vasculature, and generate an output in response to detecting the dislodgment of the elongate member from the vasculature.

25 Claims, 5 Drawing Sheets

(52) U.S. Cl.
CPC ............. *A61M 1/16* (2013.01); *A61M 1/3655* (2013.01); *A61M 2025/0002* (2013.01); *A61M 2205/0244* (2013.01); *A61M 2205/15* (2013.01); *A61M 2205/18* (2013.01); *A61M 2205/3344* (2013.01); *A61M 2205/50* (2013.01); *A61M 2205/502* (2013.01); *A61M 2205/581* (2013.01); *A61M 2230/30* (2013.01)

(58) Field of Classification Search
CPC ...... A61M 2205/0244; A61M 2205/15; A61M 2205/18; A61M 2205/3344; A61M 2205/50; A61M 2205/581; A61M 2230/30
See application file for complete search history.

(56) References Cited

U.S. PATENT DOCUMENTS

| | | | |
|---|---|---|---|
| 8,419,638 | B2 | 4/2013 | Arne et al. |
| 8,529,490 | B2* | 9/2013 | Wariar ................. A61M 1/367 604/4.01 |
| 8,920,355 | B2 | 12/2014 | Roger et al. |
| 9,352,078 | B2 | 5/2016 | Roger et al. |
| 9,622,670 | B2 | 4/2017 | Burnett et al. |
| 9,662,058 | B2 | 5/2017 | Burnett et al. |
| 10,398,857 | B2* | 9/2019 | Larson ................ A61M 5/5086 |
| 10,688,278 | B2* | 6/2020 | Beeckler ........... A61M 25/0054 |
| 2006/0064159 | A1* | 3/2006 | Porter ................ A61M 1/3655 623/1.24 |
| 2006/0116601 | A1* | 6/2006 | Glocker .................. A61B 5/03 600/561 |
| 2006/0130591 | A1* | 6/2006 | Perkins .............. A61M 1/3655 73/800 |
| 2007/0004996 | A1* | 1/2007 | Lovejoy .............. A61M 1/3656 604/4.01 |
| 2008/0108930 | A1* | 5/2008 | Weitzel ................. A61B 5/026 210/741 |
| 2013/0220907 | A1* | 8/2013 | Fulkerson ........... A61M 1/1609 210/186 |
| 2013/0274642 | A1 | 10/2013 | Soykan et al. |
| 2014/0167190 | A1 | 6/2014 | Hodgson et al. |
| 2015/0080782 | A1 | 3/2015 | Roger et al. |
| 2016/0158433 | A1 | 6/2016 | Wiktor et al. |
| 2016/0183819 | A1 | 6/2016 | Burnett et al. |
| 2016/0356667 | A1 | 12/2016 | Furmanski et al. |
| 2018/0071449 | A1 | 3/2018 | Hasegawa et al. |
| 2018/0361051 | A1 | 12/2018 | Kopperschmidt |

OTHER PUBLICATIONS

U.S. Appl. No. 16/781,035, filed Feb. 4, 2020, naming inventors Bloomberg et al.
Extended Search Report from counterpart European Application No. 20164468.9, dated Sep. 14, 2020, 8 pp.
Final Office Action from U.S. Appl. No. 16/781,035, dated May 25, 2022, 30 pp.
Response to Office Action dated Nov. 1, 2021, from U.S. Appl. No. 16/781,035, filed May 2, 2022, 15 pp.
Office Action from U.S. Appl. No. 16/781,035, dated Nov. 1, 2021, 16 pp.
Advisory Action from U.S. Appl. No. 16/781,035 dated Aug. 15, 2022, 3 pp.
Response to final Office Action dated May 25, 2022 from U.S. Appl. No. 16/781,035, filed Jul. 25, 2022, 15 pp.

* cited by examiner

MEDICAL DEVICE DISLODGMENT DETECTION

CROSS-REFERENCE TO RELATED APPLICATION

This application claims the benefit of and priority to U.S. Provisional Patent Application No. 62/834,051 filed Apr. 15, 2019, the entire disclosure of which is incorporated by reference herein.

TECHNICAL FIELD

The present disclosure relates to hemodialysis for the treatment of renal diseases.

BACKGROUND

In a hemodialysis treatment, a dialysis device is used to filter waste, salts, and fluids from blood of a patient when the kidneys of the patient are no longer able to adequately do so. During hemodialysis, two needles or other elongate members are inserted into an access site, such as an arteriovenous fistula, an arteriovenous graft, or a central vein for a catheter. An arterial needle may be fluidically coupled to an arterial line, which diverts blood from the vasculature of the patient via the access site to dialysis device. The dialysis device is configured to filter waste, salts, and fluids from the blood. A venous needle may be coupled to a venous line, which delivers blood from the dialysis device to the vasculature of the patient via the access site.

SUMMARY

This disclosure describes example devices, systems, and techniques for detecting dislodgment of a medical device from vasculature of a patient based on pressure sensed adjacent to the medical device. The medical device may be an elongate member configured to introduce blood into or remove blood from vasculature of a patient during hemodialysis. In examples described herein, a system includes an elongate member configured to be introduced into vasculature (e.g., an arteriovenous fistula or central vein) of a patient and a pressure sensor configured to generate a pressure signal indicative of pressure adjacent the elongate member. For example, the pressure sensor can be positioned on the elongate member and may be configured to be within the blood flow of the patient when the elongate member is properly positioned within the vasculature. The system also includes processing circuitry configured to receive the pressure signal from the pressure sensor and detect, based on the pressure signal, the dislodgment of the elongate member from the vasculature of the patient. The processing circuitry is configured to generate an output in response to detecting the dislodgment of the elongate member from the vasculature. The output may enable a patient, patient caretaker, and/or a clinician to monitor and promptly address dislodgment of the venous elongate member during the hemodialysis treatment.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
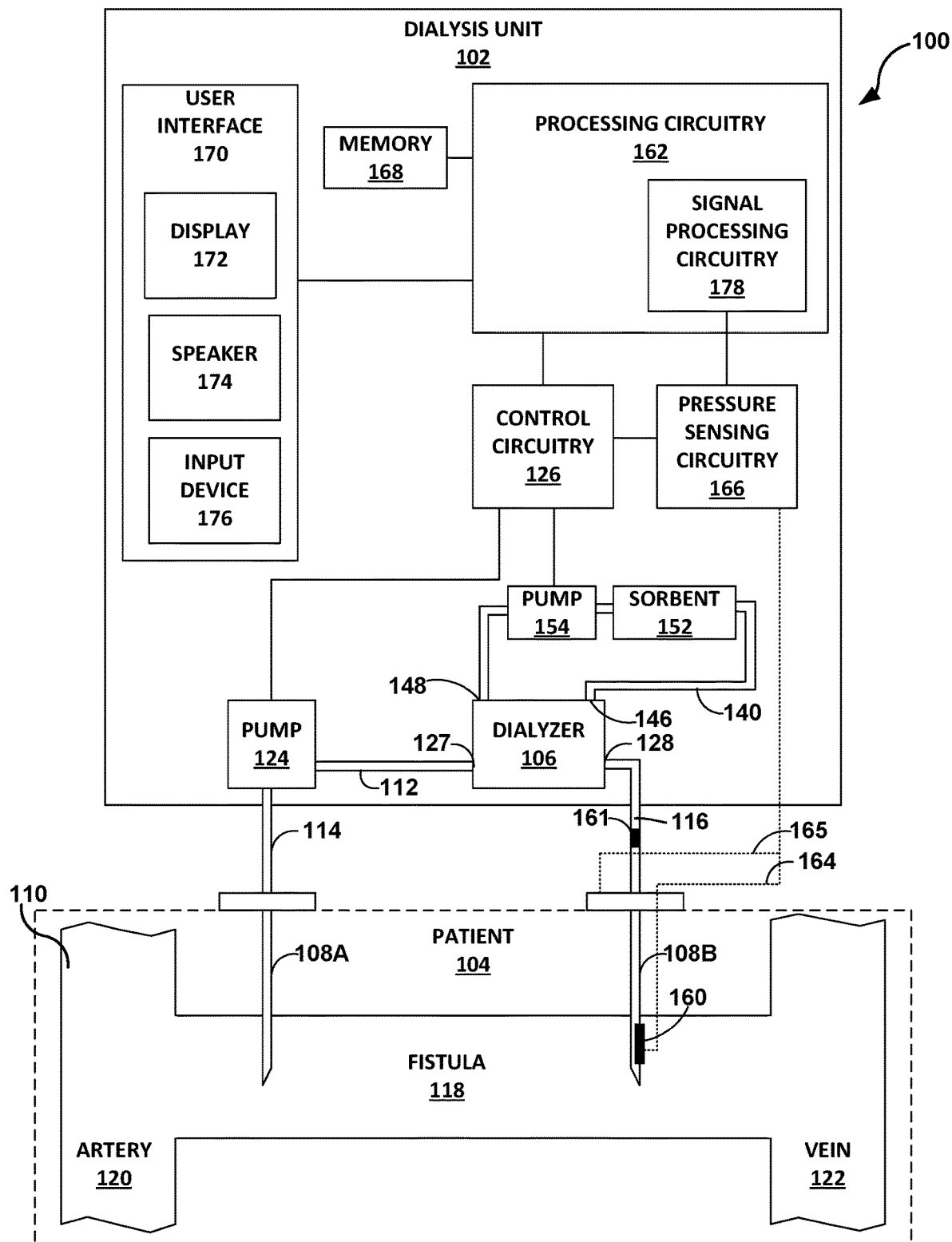
FIG. 1 is a diagram illustrating an example system configured to monitor pressure adjacent a needle in an arteriovenous fistula of a patient during hemodialysis.

Unless defined otherwise, all technical and scientific terms used generally have the same meaning as commonly understood by one of ordinary skill in the art.

The articles "a" and "an" may refer to one or more than one (e.g., at least one) of the grammatical object of the article. For example, "an element" means one element or more than one element.

The term "analog signal" may refer to any continuous signal for which the time-varying feature (variable), e.g., voltage or current, of the signal is a representation of some other time varying quantity, e.g., pressure.

The term "antithrombogenic material" may refer to a material that reduces or prevents the formation of a thrombus.

The term "arteriovenous fistula" may refer to any connection between an artery and a vein, surgically formed between a natural artery and a natural vein, with or without use of a natural graft or an artificial graft.

The term "notification" may refer to any audio, visual, or tactile notification (or combinations thereof), such as an indication of a particular state of a system or patient.

The term "at least" refers to no less than or at the minimum. For example, "at least one" could be one or any numbers more than one.

The term "capacitance" may refer to the ratio of the change in an electric charge in a system to the corresponding change in electric potential in the system.

The term "cannula" may refer to a relatively thin tube inserted into a vein or body cavity of a patient. The cannula defines a lumen through which fluids may be introduced into and removed fluids from a patient.

The term "catheter" may refer to a fluid delivery conduit, such as a tubular member, configured to be inserted into a body of a patient. A catheter defines a lumen through which fluids may be introduced into or removed from a patient. In some cases, medical devices can also be introduced into the patient or removed from the patient via a lumen of a catheter.

The term "clinician" may refer to a doctor or other medical staff having direct contact with and responsibility for a patient.

The terms "communication" or "communicatively coupled" may refer to a wired or wireless link between two components, such as an electrical connection, an optical connection, radio wave transmission and reception, or the like.

The terms "comparing," "compare," or "comparison" may refer to determining the differences, if any, between two values or other parameters.

The term "comprising" may include, but is not limited to, whatever follows the word "comprising."

The terms "determining" and "determine" may refer to ascertaining a particular state of a system or a variable.

The term "dialysis" may refer to is the process of removing excess water, solutes, and toxins from the blood in a patient whose kidneys can no longer perform these functions naturally.

The terms "dialysis system" and "dialysis unit" may refer to any medical device configured to perform dialysis.

The term "dialysate" may refer to a fluid circulated through a dialysate pathway to remove waste from the blood of a patient during hemodialysis.

The term "dialyzer" may refer to an apparatus including one or more containers for liquids separated into compartments by membranes in which dialysis is carried out.

The term "differential pressure" may refer to a quantity equal to the difference between two pressure values, such as, but not limited to, a measured pressure value and a reference pressure value.

The terms "dislodge" or "dislodgment" may refer to the movement or removal of a prosthesis, such as an elongate member, from its established position.

The term "elongate member" may refer to a needle, a cannula, a catheter, or a similar elongate medical device configured to be inserted into the vasculature of a patient. The elongate member may define a lumen through which fluids may be introduced into and removed fluids from a patient, e.g., during dialysis.

The term "execute" may mean to carry out a process or series of steps.

The term "extracorporeal circuit" may refer to the path the blood of a patient takes outside of the body during hemodialysis.

The term "fluid" may refer to a liquid phase of a substance optionally having a combination of gas and liquid phases or a gas phase of a substance optionally having a combination of gas and liquid phases.

The term "fluidically coupled" may refer to the ability to pass a fluid, such as gas, liquid, or mixtures thereof, from a first point to a second point, within or between any one or more of compartments, modules, systems, and components, all of any type.

The term "flow rate" may refer to a volume of fluid moving through a conduit or system per unit time.

The term "graft" may refer to a piece of living tissue that is transplanted surgically.

The term "hemodialysis" may refer to medical procedure or treatment to remove fluid and waste products from the blood of a patient and to correct electrolyte imbalances.

The term "intervene" may refer to any action that prevents or alters a result or a course of events.

The term "microelectromechanical systems" may refer to a device having a size in a range of about 20 micron to about 100 micron, or including components having a size in a range of about 1 micron and about 100 microns in size.

The term "monitoring" or to "monitor" may refer to determining a status of a system or patient.

The term "patient" may refer to a human patient or other mammalian or non-mammalian, non-human patients. The patient can be an apparently healthy individual, an individual with a patient condition that adversely affects a health of the patient, or an individual being treated for a patient condition.

The term "patient caretaker" may refer to any person assisting a patient.

The term "piezoelectric effect" may refer to the ability of a material to generate an electric charge in response to applied mechanical stress.

The term "piezoresistive effect" may refer to a change in the electrical resistivity of a material in response to applied mechanical stress.

The terms "pressure of a fluid" or "fluid pressure" may refer to a force exerted by a fluid.

The term "pressure sensor" may refer to any component, including circuitry, capable of determining the force exerted by a fluid.

The term "pressure wave" may refer to a wave in which the propagated disturbance is a variation of pressure in a material medium.

The term "processing circuitry" may refer to any combination of integrated circuitry, discrete logic circuitry, analog circuitry, such as one or more microprocessors, digital signal processors (DSPs), ASICs, or field-programmable gate arrays (FPGAs).

The term "reference pressure" may refer to a pressure value used as a point of reference, such as a pressure external to the vasculature of a patient or an ambient atmospheric pressure.

The term "sensor" may refer to a component including, or communicatively coupled to, processing circuitry and configured to sense one or more states of one or more variables in a system.

The term "signal" may refer to a detectable physical quantity or impulse (as a voltage, current, magnetic field strength, or electromagnetic radiation) by which information may be transmitted.

The term "signal pressure" may refer to a detectable physical quantity or impulse (as a voltage, current, magnetic field strength, or electromagnetic radiation) by which a pressure, measured by a pressure sensor, may be transmitted.

The term "solute" may refer to a substance dissolved in, or intended to be dissolved in, a solvent.

The term "solvent" may refer to a substance that is able to dissolve other substances.

The term "stenosis" may refer to an abnormal narrowing or contraction of a body passage or opening, such as an arteriovenous fistula.

The term "threshold" may refer to a predetermined value to which an analyzed parameter can be compared. Whether the analyzed parameter is greater than, equal to, or less than the threshold can direct or cause some action to be taken.

The term "threshold pressure" may refer to a predetermined value to which a pressure value, measured by a pressure sensor, can be compared.

The term "threshold rate of change" may refer to a predetermined rate of change to which a determined rate of change of a parameter can be compared.

The term "thrombus" may refer to a stationary blood clot.

The term "thrombogenic" may refer to a material that facilitates thrombosis, or otherwise contributes to formation of a thrombus.

The term "vasculature" may refer to any part of the circulatory system of the patient, such as the blood vessels of the patient, and can include an arteriovenous fistula or an arteriovenous graft.

The term "waste" may refer to urea, creatinine, uric acid, or any other component intended to be removed from the blood of the patient by hemodialysis treatment.

Devices, systems, and techniques for monitoring pressure at an elongate member, such as a needle, a cannula, or a catheter, during hemodialysis are described herein. In some examples, a system includes an elongate member configured to be introduced into vasculature of a patient, such as in an arteriovenous fistula. The elongate member may define a conduit through which blood is diverted from the vasculature to a dialysis device and/or through which blood is introduced back into the vasculature from the dialysis device. The elongate member may include a pressure sensor configured to generate a pressure signal indicative of pressure adjacent the elongate member. The system also includes processing circuitry configured to receive the pressure signal from the pressure sensor and detect dislodgment of the elongate member from the vasculature based on the pressure signal. As one example, the processing circuitry may be configured to determine the pressure adjacent the elongate member based on the pressure signal and compare the pressure adjacent the elongate member with a threshold pressure. As another example, the pressure signal may include an analog signal and the processing circuitry may be configured to determine the analog pressure signal does not include a pulse pressure wave component, the pulse pressure wave being indicative of a natural (native) pulse pressure of the patient, and detect the dislodgment of the elongate member in response to determining the analog pressure signal does not include the pulse pressure wave component.

The processing circuitry may generate an output in response to detecting the dislodgment of the elongate member from the vasculature. The output may enable a patient, patient caretaker, and/or a clinician to monitor and intervene to address dislodgment of the elongate member during hemodialysis.

During some types of hemodialysis treatment, two elongate members, such as needles, are inserted into vasculature of the patient at an access site, such as an arteriovenous fistula or an arteriovenous graft. An arterial elongate member may be fluidically coupled to an arterial line, which diverts blood from the vasculature of the patient to dialysis device, and a venous elongate member may be coupled to a venous line, which delivers blood from the dialysis device to the vasculature of the patient. In some cases, during hemodialysis, the venous elongate member may become dislodged from the arteriovenous fistula, which may result in the blood being returned from the dialysis device to be delivered into the patient outside the vasculature of the patient. If action is not taken relatively quickly to reposition the venous elongate member into the vasculature to enable the blood to be returned into the vasculature, then the venous elongate member dislodgment may result in significant blood loss.

Devices and systems described herein include a pressure sensor either on the outer or inner surface of an elongate member that is communicatively coupled to processing circuitry. The system also includes an arterial elongate member configured to be introduced into the arteriovenous fistula. In some examples, the elongate members may each include a needle and may be referred to as a venous needle and an arterial needle. While needles are primarily referred to herein, in other examples, the elongate members may include other types of elongate members through which blood may be introduced or removed from vasculature of a patient, such as, but not limited to, a cannula, a catheter, a chronic indwelling catheter, or an acute hemodialysis catheter. A dialysis unit fluidically is coupled to the venous elongate member and the arterial elongate member. The dialysis unit may be configured to dialyze a volume of fluid extracted from the vasculature (e.g., via an arteriovenous fistula) through the arterial elongate and return a volume of dialyzed fluid to the vasculature through the venous elongate member. While an arteriovenous fistula is primarily referred to herein as the access point into the vasculature of the patient, in other examples, the arterial elongate member and/or the venous elongate member may be positioned to remove or deliver, respectively, blood from the vasculature of the patient through another type of access point.

The pressure sensor may include any suitable relatively low profile pressure sensor configured to generate a signal indicative of sensed pressure. In some examples, the pressure sensor includes a microelectromechanical systems (MEMS) pressure sensor configured to be positioned on or near a venous needle, such as inside or outside the needle near the needle tip or inside the venous line near the needle and within the blood flow of the arteriovenous fistula. In some examples, the processing circuitry is configured to detect the dislodgment of the needle by at least comparing the pressure adjacent the needle with a threshold pressure. For example, the processing circuitry is configured to detect the dislodgment of the needle in response to determining the pressure adjacent the needle is less than or equal to the threshold pressure. The threshold pressure may include at least one of lower than a predetermined nominal fistula pressure or greater than an atmospheric pressure.

In some examples, processing circuitry of a system described herein may calibrate the pressure sensor or otherwise calibrate the devices and systems described herein with the pressure sensor in ambient atmospheric conditions before the patient is cannulated. For example, the processing circuitry may calibrate the baseline gauge pressure to 0 mmHg with respect to the room in which dialysis is being performed. The threshold pressure may be based on this calibration, e.g., at least about 10 mmHg under which the dislodgment signal would be triggered by the processing circuitry. In some examples, the processing circuitry is configured to detect the dislodgment of the needle by at least detecting a sudden and sustained change in pressure. For example, the processing circuitry may be configured to determine a rolling average pressure measurement, such as, but not limited to, a 2 second to 10 second (e.g., 5 second) rolling average pressure measurement. The processing circuitry may determine a pressure signal change, based on the rolling average pressure measurement, such as a pressure change between a previous rolling average pressure value and a current rolling average pressure value of more than about 10% to about 20%, such as about 15%. The processing circuitry may determine a duration over which the pressure remains at the current rolling average value, such as for more than 0.25 seconds to about 1 second, such as 0.5 seconds, (e.g., to filter out sudden spikes caused by movement). In some examples, the processing circuitry may determine that the sudden and sustained change in pressure is classified as a dislodgement event.

In some examples, the processing circuitry is configured to receive an analog pressure signal from the MEMS pressure sensor. When the venous needle is properly positioned within the blood flow in the vasculature of the patient, an analog pressure signal may be indicative of a "true fistula pressure," such as a pressure between about 20 millimeters of mercury (mmHg) and about 100 mmHg, which may be distinguishable from typical atmospheric pressure of about 760 mmHg. For example, the analog pressure signal may be generated by a pressure sensor positioned directly on the outside of the tip of the needle and within the blood flow in the arteriovenous fistula. The analog pressure signal may include a pulse pressure wave component, e.g., indicative of the natural pulse pressure of the patient, and a hemodialysis device peristaltic pump pressure wave component. In some examples, the processing circuitry may separate the patient's natural pressure pulse wave from the hemodialysis peristaltic pump pressure wave, such as by using a filter that filters out the known hemodialysis peristaltic pump pressure wave from the analog pressure signal. The processing circuitry may be configured to determine the analog pressure signal does not include a pulse pressure wave component and detect the dislodgment of the needle in response to determining the analog pressure signal does not include the pulse pressure wave component.

The processing circuitry may generate an output in response to detecting the dislodgment of an elongate member from the arteriovenous fistula. In some examples, the processing circuitry may be configured to generate the output by at least controlling the dialysis unit. For example, the processing circuitry may be configured to control the dialysis unit by at least causing a dialysis pump of the dialysis unit to stop extracting fluid from the arteriovenous fistula. In some examples, after determining dislodgement of the needle, the processing circuitry may cause the dialysis unit stop blood intake by, for example, clamping off the venous line and/or arterial line, stopping the blood pump, or both. Causing the dialysis pump to stop extracting fluid from the vasculature of the patient, or otherwise stopping blood intake, may reduce an amount of blood drawn from the patient when the blood may not be properly returned to the vasculature of the patient due to venous needle dislodgment. In this way, the processing circuitry may be configured to modify an operation of the dialysis unit in response to detecting dislodgement of a venous needle. In addition to or instead of controlling the dialysis unit, in some examples, the processing circuitry may be configured to generate the output by at least presenting a notification via a user interface that instructs a user to reposition the needle in the arteriovenous fistula, to stop the dialysis unit, or the like.

In some cases, the health of an arteriovenous fistula of a patient may change over time due to a stenosis or other change to the patency of the arteriovenous fistula or vasculature near the arteriovenous fistula. In some examples, the pressure adjacent the needle within the vasculature of the patient may be associated with fistula health. For example, fistula health may be associated with the available flow in the fistula, which can be directly correlated with the pressure in the fistula. As one example, a patient with a thrill may have a mean systolic pressure of about 35.8 mmHg and a systolic-diastolic pressure gradient of about 3.4 mmHg. A thrill may include a sensation similar to a vibration, which indicates blood flow through the fistula, and indicates the fistula has proper blood flow. A patient without a thrill may have a mean systolic pressure of about 102.6 mm Hg and a systolic-diastolic pressure gradient of about 42.8 mmHg. The lack of a thrill may indicate reduced blood flow in the fistula and, possibly an obstruction in the fistula. As illustrated by way of this example, patients with an obstruction in the fistula may have a higher venous pressure in the fistula compared to patents without an obstruction in the fistula.

Measurement of fistula pressures via an elongate member including a pressure sensor, as described herein, may be useful for detecting changes in the patency of arteriovenous fistulas. For example, the processing circuitry may be configured to detect a venous stenosis in the arteriovenous fistula based on the pressure signal. In some examples, the processing circuitry may be configured to detect the venous stenosis in response to determining the pressure adjacent the needle is greater than or equal to a threshold pressure. In some examples, the processing circuitry may be configured to detect the venous stenosis in response to determining a rate of pressure change adjacent the needle is greater than or equal to a predetermined threshold rate of pressure change. For example, the processing circuitry may be configured to detect the venous stenosis by at least determining a flow rate through the arteriovenous fistula based on the pressure signal; detecting a threshold pressure change in the arteriovenous fistula based on the pressure signal; detecting a threshold flow rate change in the arteriovenous fistula based on the determined flow rate, e.g., determined from the integral of the arterial and venous pressure signals; and detecting the venous stenosis in the arteriovenous fistula in response to detecting the threshold pressure change and the threshold flow rate change.

In some examples, absolute pre-treatment, intra-dialytic, and post-treatment pressures and flow-rates (derived from pressure signals) may be used to establish a baseline for each patient. Changes from these baseline values may be used to estimate physiologic states. For example, disconnects of a fistula needle or catheter from a dialysis system may manifest as sudden drop in intra-elongate pressure or flow which may be defined relative to each patient's established baseline values. Acquired pressure signals may be transmitted to a dialysis machine or another device for processing and storage. For example, processing circuitry of the dialysis machine (or a hand-held or body-worn receiving and processing unit) may use one or more algorithms to direct action including but not limited to stopping a dialysis treatment, sounding an alarm on the dialysis machine or patient's hand-held device and instructing patient to seek immediate care for outcomes such as a disconnect.

Sensing the venous pressure at the venous needle during hemodialysis treatment may help improve dialysis treatment outcomes for patients. For example, the outcomes may include reduction of hypotension during and immediately after cessation of treatment, monitoring of recirculation within the circuit, monitoring of dislodgement of access needles/cannula or catheter, and/or monitoring of occlusion in the vascular access site, which in turn can lead to loss of dialysis treatment, hospitalizations, or interventional procedures. In some examples, the processing circuitry may be configured to modify an operation of the dialysis unit in response to detecting the venous stenosis, such as to increase a water content of the dialysis solution. In some examples, a model of fistula health may be constructed using fistula flow measurements over time, e.g., without doppler ultrasound testing, such that when the fistula flowrate starts to decrease, clinical intervention can be taken, including but not limited to treatment of the fistula or other site with a percutaneous transluminal angioplasty (PTA) balloon.

While venous pressure may be monitored in an extracorporeal circuit with a pressure monitor located in a hemodialysis device, the venous pressure at the environment around the tip of an elongate member inside the vasculature may be similar enough to atmospheric pressure such that, when venous needle dislodgment occurs, the pressure measured in the hemodialysis device may not change significantly. In contrast to measuring venous pressure in the external hemodialysis device, the disclosure describes sensing pressure adjacent the elongate member within the vasculature of the patient to detect even small changes in pressure at the elongate member tip (e.g., needle tip) and/or detection of dislodgment by determining if an analog signal of the pressure signal include a pulse pressure wave. In this way, the described devices, systems, and techniques may be used to more accurately detect venous needle dislodgment compared to other devices, systems, and techniques that include a pressure sensor that is intended to be outside of the vasculature of the patient to detect the elongate member dislodgment.

FIG. 1 is a diagram illustrating an example dialysis system 100 configured to provide patient 104 with hemodialysis treatment. Patient 104 includes a human patient, although, in some examples, patient 104 may include other mammalian or non-mammalian, non-human patients. Dialysis system 100 includes dialysis unit 102, arterial line 114 including arterial needle 108A, and venous line 116 including venous needle 108B. Arterial needle 108A and venous needle 108B (collectively, "needles 108") are configured to be introduced into arteriovenous fistula 118. Arteriovenous fistula 118 may include a surgically created connection or passageway between an artery 120 and a vein 122 of patient 104. For example, the surgically created connection or passageway may be formed by grafting a portion of artery 120 directly to a portion of vein 122 or grafting a portion of a vein from a different portion the body of patient 104 between artery 120 and vein 122. In some examples, arteriovenous fistula 118 may include other structures, such as an arteriovenous graft. In some examples, the arterial line 114 and/or the venous line 116 connect directly to vasculature 110, for example, directly to artery 120 and/or vein 122, via a central venous catheter.

Dialysis unit 102 may fluidically couple to venous needle 108B and arterial needle 108A via extracorporeal circuit 112. In this way, dialysis unit 102 is configured to circulate blood of patient 104 and a dialysate through dialyzer 106. For example, dialyzer 106 may include a plurality of hollow fibers having walls defining a semipermeable membrane. The blood may flow through the plurality of hollow fibers and the dialysate may flow on the outside of the plurality of hollow fibers, e.g., counter-current relative to flow of the blood.

Locomotive power for moving the blood through the extracorporeal circuit 112 is provided by a blood pump 124. Blood pump 124 may be located along the arterial line 114. Blood may be conveyed by blood pump 124 through extracorporeal circuit 112 at any blood flow rate suitable for a hemodialysis procedure, such as, but not limited to, a rate of about 50 milliliters per minute (mL/min) to about 600 mL/min. In some examples, this blood flow rate may be controlled by control circuitry 126. In some examples, blood pump 124 includes a peristaltic pump. In other examples, blood pump 124 may include other types of pumps, such as a diaphragm pump, a centrifugal pump, or a shuttle pump. In some examples, the blood pump 124 conveys blood through the dialyzer 106 where the blood is contacted with a blood side of a high permeability dialysis membrane. Blood enters the dialyzer 106 through a blood inlet 127 and exits through a blood outlet 128.

Dialysate may be conveyed through one of a dialysate circuit 140 in a dialysate circuit 140, which carries dialysate to the dialyzer 106. A concentration gradient of solutes in the blood and dialysate may be established such that dialyzer 106 is configured to allow waste, salts, and fluids to be transferred from the blood in extracorporeal circuit 112 to the dialysate. For example, dialysate that is conveyed through dialyzer 106 on the dialysate side of the dialysis membrane picks up waste produces from the blood, including urea, by diffusion, hemofiltration, or hemodiafiltration. Dialysate enters dialyzer 106 at a dialysate inlet 146 and exits at an outlet 148. The dialysate is conveyed through a sorbent cartridge 152 to remove waste products before being re-conveyed through the dialyzer 106.

The dialysate is moved along the dialysis circuit 140 by a dialysate pump 154. The dialysate pump can be operated at any suitable rate, such as, but not limited to, a rate from about 10 mL/min to about 400 mL/min. The specific rate may be dependent on the rate of the blood pump 124 at the desired contact time with the dialysis membrane to achieve diffusion of impurities from blood to the dialysate. In some examples, dialysate flow rate may be controlled by control circuitry 126.

By passing blood and dialysate through dialyzer, dialysis unit 102 may be configured to dialyze a volume of fluid extracted from arteriovenous fistula 118 through arterial needle 108A and return a volume of dialyzed fluid to the arteriovenous fistula through venous needle 108B. The portion of extracorporeal circuit 112 that contains drawn blood from the patient can be referred to as the arterial line 114, which refers to a line for transporting blood from patient 104 regardless of whether blood is drawn from an artery or vein of patient 104. Similarly, the portion that returns blood to the patient can be referred to as the venous line 116.

Dialysis system 100 includes a pressure sensor configured to generate a pressure signal indicative of pressure adjacent at least one needle of needle 108. For example, venous needle 108B may include a pressure sensor 160 configured to generate a pressure signal indicative of pressure adjacent the portion of the needle within vasculature 110 of the patient. In some examples, pressure sensor 160 is positioned along an inner surface of venous needle 108B defining a lumen. In addition to or instead of the inner surface, in some examples, pressure sensor 160 is positioned along an outer surface of venous needle 108B or embedded in a surface of venous needle 108B. Whether positioned on the inner surface, outer surface, or embedded in a surface of venous needle 108B, pressure sensor 160 is configured to be positioned within the blood flow of arteriovenous fistula 118 when venous needle 108B is properly positioned within fistula 118 to return blood into fistula 118 from dialysis device 102.

Pressure sensor 160 may include any suitable pressure sensor, such as, but not limited to, a relatively low profile pressure sensor or a MEMS pressure sensor. For example, pressure sensor 160 may include an air gap capacitive sensor including two conductive plates separated by a relatively small air gap, a piezoelectric sensor including a section of material or a film coating that is configured to generate an electrical signal in response to mechanical stress, or a strain gauge/MEMS cantilever strain gauge type sensor, any of which may, in some examples, be constructed using wafer scale manufacturing techniques. In some examples, pressure sensor 160 may include passive circuitry components (inductors, resistors, and capacitors) and not include active circuitry components. A relatively low profile pressure sensor may have a profile that does not substantially impede blood flow within or around venous needle 108B, e.g., compared to a venous needle without pressure sensor 160, and/or reduced the potential for thrombus formation on or near pressure sensor 160. In some examples, pressure sensor 160 may include dimensions, such as length, wide, and height, that are each between about 0.1 micrometers and about 1 millimeter. In some examples, pressure sensor 160 may include a silicon chip based MEMS pressure sensor. The MEMS pressure sensor may be sufficiently small to be attached to a tip of venous needle 108B, or housed in a casing attached to a tip of venous needle 108B, without substantially impeding blood flow within or around venous needle 108B, which may help reduce the potential for thrombus formation due to the presence of pressure sensor 160 in the blood flow, or both. For example, a MEMS pressure sensor may have a size (length, width, and/or height) in a range of about 20 nanometers to about 1 micron, or including components having a size in a range of about 1 nanometer and about 1 micron in size. The entire pressure sensor assembly can be larger, for example 1 mm×1 mm×1 mm, although other sized sensors can also be used.

In some examples, pressure sensor 160 may include signal processing circuitry, e.g., pressure sensing circuitry 166, a pressure sensing member, or both. The pressure sensing member may operate by, for example, a change in capacitance, piezoelectric effect, or piezoresistive effect in response to an applied pressure. In these examples, pressure sensor 160 may be configured to generate a pressure signal based on the change in capacitance, piezoelectric effect, or piezoresistive effect. As discussed in greater detail below, pressure sensing circuitry 166 may be configured to relay or pre-process a pressure signal.

Pressure sensor 160 may include a passive sensor or an active sensor. A passive pressure sensor 160 may not be directly coupled to a power source. For example, a passive pressure sensor 160 may be powered by, for example, induction via a magnetic field generated by a device external to passive pressure sensor 160 or other electromagnetic or indirect power sources. In some examples, a passive pressure sensor 160 is not electrically coupled to any wires or wires that extend along a length of needle or other elongated device, such as a cannula or a catheter. An active pressure sensor 160 may be powered by its own power source, such as a battery.

To help reduce the impact of pressure sensor 160 on the operation of system 100 or to help protect a reduction in the integrity of pressure sensor 160 from environmental factors, in some examples, pressure sensor 160 may include a materials, applied as a casing, a coating, embedded in the pressure sensor 160, or any other suitable application, such as, for example, a biocompatible material, silicones, parylenes (e.g., poly(p-xylene)-based polymers), antithrombogenic materials, platelet aggregation inhibitors, or the like. Example antithrombogenic materials or platelet aggregation inhibitors include, but are not limited to, 2-Methacryloyloxyethyl phosphorylcholine (MPC, available as LIPIDURE™ from NOF Corporation of Tokyo, Japan); PARYLENE C™, or PARYLENE HT™, both available from Specialty Coating Systems of Indianapolis, Ind.; BAY-MEDIX™ available from Bayer AG of Leverkusen, Germany; BIOCOAT™ hyaluronic acid available from Bio-Coat, Inc. of Horsham, Pa.; or polyethylene oxide; heparin, heparin-like materials or derivatives, hirudin, H-Heparin, HSI-Heparin, albumin, phospholipids, streptokinase, tissue plasminogen activator (TPA), urokinase, hyaluronic acid, chitosan, methyl cellulose, poly(ethylene oxide), poly(vinyl pyrrolidone), endothelial cell growth factor, epithelial growth factor, osteoblast growth factor, fibroblast growth factor, platelet derived growth factor or angiogenic growth factor. The casing and/or coating may reduce thrombogenic surfaces of pressure sensor 160 and/or hermetically seal pressure sensor 160.

In some examples, dialysis system 100 may include a reference pressure sensor 161. Reference pressure sensor 161 may be configured to generate a reference pressure signal indicative of a pressure external to vasculature 110 of patient. For example, reference pressure sensor 161 may be positioned on a portion of venous needle 108B configured to be external to fistula 118 when pressure sensor 160 is located within fistula 118 or any other portion of dialysis system 100 external to vasculature 110, such as, for example, a portion of venous line 116 or an external surface of dialysis unit 102. In some cases, reference pressure sensor 161 may have the same or substantially similar configuration as pressure sensor 160 described above. In some examples, rather than detecting dislodgment of needle 108B based on pressure sensed by pressure sensor 160 alone, processing circuitry 162 may use both the pressure signal generated by pressure sensor 160 and a reference pressure signal generated by reference pressure sensor 161. For example, processing circuitry 162 may determine a differential pressure by at least determining a difference between a pressure adjacent to venous needle 108B and the atmosphere outside the body of patient 104. By determining a differential pressure, dialysis system 100 may be configured to determine absolute pressure or a relative pressure (e.g., relative to ambient pressure) within arteriovenous fistula 118. Processing circuitry 162 may use this absolute or relative pressure may be used to detect dislodgment of needle 108B, such as by detecting an absolute or relative pressure less than or equal to a predetermined threshold or by detecting a rate of change of the absolute or relative pressure that is above a predetermined rate of change.

Dialysis system 100 is configured to receive the pressure signal from pressure sensor 160. For example, pressure sensor 160 may be communicatively coupled to processing circuitry 162 via any suitable connection 164, such as a wired connection, a wireless connection, or a combination of both. In some examples, a wired connection may include an electrical cable or optical fiber extending within a lumen of venous line 116, external to venous line 116, or a combination of both. For example, wired connection 164 may be integrally formed with at least a portion of venous needle 108B or fixed to an inner or outer surface of venous needle 108B by, for example, a biocompatible material, silicones, or parylenes. In some examples, a wireless connection may include passive or active radio frequency communication, such as near-field radio frequency, Bluetooth™, WiFi™, or the like. For example, pressure sensor 160 may include communication circuitry configured to wirelessly communicate with an external device, such as dialysis unit 102, e.g., processing circuitry 162, a network device communicatively coupled to dialysis unit 102, e.g., processing circuitry 162, or inductively coupled via an external cuff that is worn around the location of the access point. In some examples, a wireless connection may include communication using an electrically conductive fluid, such as the blood of the patient, as a conductor. For example, pressure sensor 160 may include communication circuitry configured to wirelessly communicate with a receiving device imbedded in a lumen of venous line 116, such that the receiving device in fluid contact with the blood on one side and connected with a wire connection or wireless connection to dialysis unit 102, e.g., processing circuitry 162. In this way, pressure sensor 160 may be configured to generate a pressure signal and transmit the pressure signal to processing circuitry 162.

Processing circuitry 162, as well as other processors, processing circuitry, controllers, control circuitry, and the like, described herein, may include one or more processors. Processing circuitry 162 may include any combination of integrated circuitry, discrete logic circuitry, analog circuitry, such as one or more microprocessors, digital signal processors (DSPs), ASICs, or field-programmable gate arrays (FPGAs). In some examples, processing circuitry 162 may include multiple components, such as any combination of one or more microprocessors, one or more DSPs, one or more ASICs, or one or more FPGAs, as well as other discrete or integrated logic circuitry, and/or analog circuitry.

Control circuitry 126 may be operatively coupled processing circuitry 162. Control circuitry 126 is configured to control an operation of pressure sensor 160. In some examples, control circuitry 126 may be configured to provide timing control signals to coordinate an operation of pressure sensor 160. For example, pressure sensing circuitry 166 may receive from control circuitry 126 one or more timing control signals, which may be used by pressure sensing circuitry 166 to turn on and off pressure sensor 160.

In some examples, processing circuitry 162 may use the timing control signals to operate synchronously with pressure sensing circuitry 166. For example, processing circuitry 162 may synchronize the operation of an analog-to-digital converter and a demultiplexer with pressure sensing circuitry 166 based on the timing control signals. Although control circuitry 126 is shown as being part of dialysis unit 102, in other examples, control circuitry 126 can be incorporated into a device separate from dialysis unit 102.

Memory 168 may be configured to store data, such as, for example, monitored physiological parameters, such as pressure values or blood flow rates; operational values associated with dialysis unit 102, such as operational speed of pumps 124 and 154, pressure values, or oxygen detection values, and threshold values. In some examples, memory 168 may store program instructions, such as pump startup procedures or pump shutdown procedures. The program instructions may include one or more program modules that are executable by processing circuitry 162. When executed by processing circuitry 162, such program instructions may cause processing circuitry 162 to provide the functionality ascribed to it herein. The program instructions may be embodied in software, firmware, and/or RAM ware. Memory 168 may include any one or more of volatile, non-volatile, magnetic, optical, or electrical media, such as a random access memory (RAM), read-only memory (ROM), nonvolatile RAM (NVRAM), electrically-erasable programmable ROM (EEPROM), flash memory, or any other digital media.

User interface 170 may include a display 172, a speaker 174, and an input device 176. In some examples, user interface 170 may include fewer or additional components. User interface 170 may be configured to present information to a user (e.g., patient 104, patient caretaker, or a clinician). For example, user interface 170 and/or display 172 may include a monitor, cathode ray tube display, a flat panel display such as a liquid crystal (LCD) display, a plasma display, a light emitting diode (LED) display, and/or any other suitable display. In some examples, user interface 170 may be part of a multiparameter monitor (MPM) or other physiological signal monitor used in a clinical or other setting, a personal digital assistant, mobile phone, tablet computer, laptop computer, any other suitable computing device, or any combination thereof, with a built-in display or a separate display.

In some examples, processing circuitry 162 may be configured to present, by user interface 170, such as display 172, a graphical user interface to a user. The graphical user interface may include indications of values of one or more physiological parameters of a patient, such as, for example, blood pressure values, blood flow value, or other patient physiological parameters, and/or may include information about an operation of dialysis unit 102, other hemodialysis treatment information, a notification in response to detecting venous needle dislodgment, instructions in response to detecting venous needle dislodgment, or combinations thereof via display 172. User interface 170 may also include means for projecting audio to a user, such as speaker 174.

In some examples, processing circuitry 162 may also receive input signals from additional sources (not shown), such as a user. For example, processing circuitry 162 may receive from input device 176, such as a keyboard, a mouse, a touch screen, buttons, switches, a microphone, a joystick, a touch pad, or any other suitable input device or combination of input devices, an input signal. The input signal may contain information about patient 104, such as physiological parameters, treatments provided to patient 104, operations for controlling dialysis unit 102, e.g., received in response to user interface 170 presenting a notification about venous needle dislodgment to a user, or the like. Additional input signals may be used by processing circuitry 162 in any of the determinations or operations it performs.

Pressure sensing circuitry 166 may be configured to receive pressure signals sensed from pressure sensor 160 via connection 164. Pressure sensing circuitry 166 may communicate the pressure signals to processing circuitry 162. In some examples, pressure sensor 160 may include pressure sensing circuitry 166. In some examples, pressure sensing circuitry 166 may be incorporated in an external device communicatively coupled to pressure sensor 160 and/or processing circuitry 162. Although pressure sensing circuitry 166 is shown as being part of dialysis unit 102, in other examples, pressure sensing circuitry 166 can be incorporated into a device separate from dialysis unit 102.

In some examples, pressure sensing circuitry 166 and/or processing circuitry 162 may include signal processing circuitry 178 configured to perform any suitable analog conditioning of the sensed physiological signals. For example, pressure sensing circuitry 166 may communicate to processing circuitry 162 an unaltered (e.g., raw) signal. Processing circuitry 162, e.g., signal processing circuitry 178, may be configured to modify a raw signal to a usable signal by, for example, filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. In some examples, the conditioned analog signals may be processed by an analog-to-digital converter of signal processing circuitry 178 to convert the conditioned analog signals into digital signals.

In some examples, signal processing circuitry 178 may operate on the analog or digital form of the signals to separate out different components of the pressure signals. In some examples, signal processing circuitry 178 may perform any suitable digital conditioning of the converted digital signals, such as low pass, high pass, band pass, notch, averaging, or any other suitable filtering, amplifying, performing an operation on the signal, performing any other suitable digital conditioning, or any combination thereof. In some examples, signal processing circuitry 178 may remove ambient contributions to the received pressure signal. Additionally, or alternatively, pressure sensing circuitry 166 may include signal processing circuitry 178 to modify one or more raw pressure signals and communicate to processing circuitry 162 one or more modified pressure signals.

Processing circuitry 162 may be configured to receive pressure signals generated by pressure sensor 160 via pressure sensing circuitry 166 and/or signal processing circuitry 178, and detect, based on the pressure signal, dislodgment of venous needle 108B from arteriovenous fistula 118. In some examples, processing circuitry 162 is configured to determine pressure adjacent venous needle 108B based on the pressure signal and detect dislodgment of venous needle 108B by at least comparing the pressure adjacent venous needle 108B with a threshold pressure. For example, processing circuitry 162 may determine the pressure adjacent to the needle based on a peak, a median, or a lowest amplitude of the pressure signal. Additionally, or alternatively, processing circuitry 162 may be configured to apply an algorithm, e.g., stored in memory 168, defining a pre-determined association between the pressure signals and the pressure adjacent the needle. In some examples, the algorithm may be periodically updated based on a calibration of pressure sensor 160.

In some examples, processing circuitry 162 is configured to detect the dislodgment of venous needle 108B in response to determining the pressure adjacent venous needle 108B is less than or equal to the threshold pressure. In some examples, processing circuitry 162 is configured to detect the dislodgment of venous needle 108B in response to determining a differential pressure (e.g., based on a pressure signal and a reference pressure signal. The threshold pressure may include any suitable threshold pressure indicative of venous needle 108B being outside of the blood flow in fistula 118. In some examples, the threshold pressure may be at least one of lower than a predetermined nominal fistula pressure or greater than an atmospheric pressure (e.g., about 760 mmHg, absolute pressure). The predetermined nominal fistula pressure may be between about 20 mmHg (gauge pressure) and about 100 mmHg (gauge pressure). For example, the threshold pressure may be less than about 20 mmHg (gauge pressure), such as between about 0 mmHg (gauge pressure) and about 20 mmHg (gauge pressure) or between about 5 mmHg (gauge pressure) and about 15 mmHg (gauge pressure). In some examples, the threshold pressure may be determined as a function of a pressure signal generated by pressure sensor 160 (alone or in combination with circuitry 166). For example, the threshold pressure may be a percentage of a baseline pressure signal that indicates pressure sensed when venous needle 108B was known to be within the blood flow of fistula 118. Additionally, or alternatively, the threshold pressure may include a rate of change (e.g., decrease) in the baseline pressure signal. The threshold pressure, the baseline pressure signal, or other metrics used by processing circuitry 162 to detect needle dislodgment may be stored by memory 168.

In some examples, the pressure signal generated by pressure sensor 160 and received by processing circuitry 162 may include an analog pressure signal. The analog pressure signal may be indicative of an analog pressure wave that includes a pulse pressure wave component, e.g., indicative of the pulse pressure of patient 104 (also referred to herein as the "natural" pulse pressure), and a pump pressure wave component, e.g., indicative of the pulse pressure of pump 124. Processing circuitry 162 may be configured to detect dislodgment of venous needle 108B in response to determining the analog pressure signal does not include the pulse pressure wave component. The analog pressure signal not including the pulse pressure wave component can indicate that venous needle 108B is not fluidically coupled to vasculature 110, which indicates that venous needle 108B may no longer be properly positioned within fistula 118 to deliver blood back into fistula 118, and, therefore, dislodged from fistula 118. In some examples, processing circuitry 162 may determine the analog pressure signal does not include the pulse pressure wave component by at least detecting the pump pressure wave component in the analog pressure signal, generating a residual wave by at least filtering out the pump pressure wave component from the analog pressure signal, and determining the residual wave does not include the pulse pressure wave component. The pump pressure wave may be easier to characterize compared to the pulse pressure wave, e.g., due to consistency of operation of pump 124, such that filtering the pump pressure wave component from the analog pressure signal may be less computationally intensive than identifying the pulse pressure wave component in the unfiltered analog pressure signal.

Processing circuitry 162 is configured to generate an output in response to detecting the dislodgment of one of the needles 108 from arteriovenous fistula 118. In some examples, if processing circuitry 162 determines that one needle of needles 108 has dislodged, then processing circuitry 162 may generate the output by at least presenting a notification via user interface 170 indicating the potential needle dislodgment. In some examples, the notification may instruct a user (e.g., patient 104, patient caretaker, or a clinician) to check the position of needles 108 and, if necessary, reposition needles 108 in the arteriovenous fistula 118 or to stop dialysis unit 102 and notify a clinician. In some examples, processing circuitry 162 and user interface 170 may be part of the same device or supported within one housing (e.g., a computer or monitor). In other examples, processing circuitry 162 and user interface 170 may be separate devices configured to communicate through a wired connection or a wireless connection (e.g., a communication interface).

In some examples, in addition to or instead of the notification to a user presented via user interface 170, processing circuitry 162 may be configured to generate the output by at least controlling dialysis unit 102 based on the detection of the dislodgment of venous needle 108B (or arterial needle 108A in other examples) from arteriovenous fistula 118. For example, processing circuitry 162 may control dialysis unit 102 by at least causing pump 124 to stop extracting fluid from arteriovenous fistula 118 via arterial needle 108A. In some examples, processing circuitry 162 may cause pump 124 to stop extracting fluid by executing a pump shutdown procedure, e.g., a pump shutdown procedure stored in memory 168 and executed by processing circuitry 162 via control circuitry 126, or closing a valve positioned in arterial line 114 between arterial needle 108A and pump 124. By automatically stopping dialysis unit 102 from extracting fluid from arteriovenous fistula 118, dialysis system 100 may reduce blood loss during venous needle 108B dislodgement.

In some examples, processing circuitry 162 may be configured to determine that venous needle 108B is no longer dislodged, e.g., by determining that pressure signal is no longer less than a threshold value or by user input confirming venous needle 108B is not dislodged, and automatically control dialysis unit 102 to resume extracting fluid from arteriovenous fistula 118, e.g., by executing a pump startup procedure or opening the valve positioned in arterial line 114. By automatically resuming extraction of fluid from arteriovenous fistula 118, dialysis system 100 may reduce dialysis treatment time, reduce use of clinical resources, or both.

A pressure signal generated by pressure sensor 160 may be used to detect other conditions that may impact the outcome of a dialysis treatment. For example, in addition to or instead of detecting dislodgment of an elongated member from arteriovenous fistula 118 or other part of vasculature of a patient, in some examples, processing circuitry 162 is configured to detect a venous stenosis in arteriovenous fistula 118 based on the pressure signal generated by pressure sensor 160. Venous stenosis in arteriovenous fistula 118 may include narrowing of arteriovenous fistula 118 and obstruction of adequate blood flow to properly perform dialysis treatment using arteriovenous fistula 118. This obstruction of blood flow may present as a change in blood pressure sensed by pressure sensor 160 disposed within arteriovenous fistula 118. In some examples, processing circuitry 162 may detect venous stenosis in response to determining that the pressure adjacent venous needle 108B is greater than or equal to a threshold pressure, e.g., a venous stenosis threshold pressure. In some examples, the venous stenosis threshold pressure is a pressure value that is known to indicate a desirable level of patency in vasculature for dialysis, and can be determined based on sensed parameters of patient 104 or sensed parameters for a population of subjects that may or may not include patient 104. For example, for some patients, the venous stenosis threshold pressure may be a pressure greater an about 40 mmHg to about 100 mmHg, such as a systolic pressure greater than about 100 mmHg and/or a diastolic pressure greater than about 40 mmHg.

In some examples, processing circuitry 162 may detect venous stenosis in response to determining a change in the pressure adjacent venous needle 108B over time is greater than or equal to a threshold rate of pressure change. In some examples, the venous stenosis threshold rate of pressure change is a rate value that is known to indicate a desirable level of patency in vasculature for dialysis, and can be determined based on sensed parameters of patient 104 or sensed parameters for a population of subjects that may or may not include patient 104. For example, for some patients, the venous stenosis threshold rate of pressure change may be a rate greater about 10% to about 20% change in a previously sensed pressure value, which may be a rolling average pressure value, as discussed above.

In some examples, processing circuitry 162 may be configured to detect the venous stenosis by at least determining a flow rate through arteriovenous fistula 118 based on the pressure signal generated by pressure sensor 160. Processing circuitry 162 may detect a threshold flow rate change in arteriovenous fistula 118 based on the determined flow rate. Processing circuitry 162 also may detect a threshold pressure change in arteriovenous fistula 118 based on the pressure signal. Processing circuitry 162 may detect the venous stenosis in arteriovenous fistula 118 in response to detecting the threshold pressure change and the threshold flow rate change. For example, a reduced flow rate and increased pressure may indicate an obstruction in arteriovenous fistula 118 indicative of venous stenosis in arteriovenous fistula 118.

In some examples, processing circuitry 162 may be configured to modify an operation of dialysis unit 102 in response to detecting the venous stenosis. For example, processing circuitry 162 may control, via control circuitry 126, pump 124 to reduce the flow rate of blood through extracorporeal circuit 112. Reducing the flow rate of blood through extracorporeal circuitry 112 may reduce the pressure in arteriovenous fistula 118. Reducing the pressure in arteriovenous fistula 118 may reduce adverse effects to vasculature 110 due to hemodialysis.

While the example of FIG. 1 is primarily described with reference to detecting dislodgment of venous needle 108B from fistula 118, in other examples, the same or similar techniques may be used by processing circuitry 162 to detect dislodgment of arterial needle 108A from fistula and generate an output indicative of the arterial needle dislodgment. Automatic detection of arterial needle dislodgment may help improve the efficiency of a dialysis session by helping to ensure blood is being withdrawn from patient 104 at a desirable rate for an efficient dialysis session.

Dialysis device 102 is described with respect to FIG. 1 as having a specific configuration. In other examples, dialysis device 102 may have another suitable configuration and may operate using other dialysis principles. The detection of elongate member dislodgment using the devices, systems, and techniques described herein are applicable to any suitable dialysis technique, as well as to other medical procedures that includes withdrawing and introducing blood into vasculature of a patient.

Figure 2A:
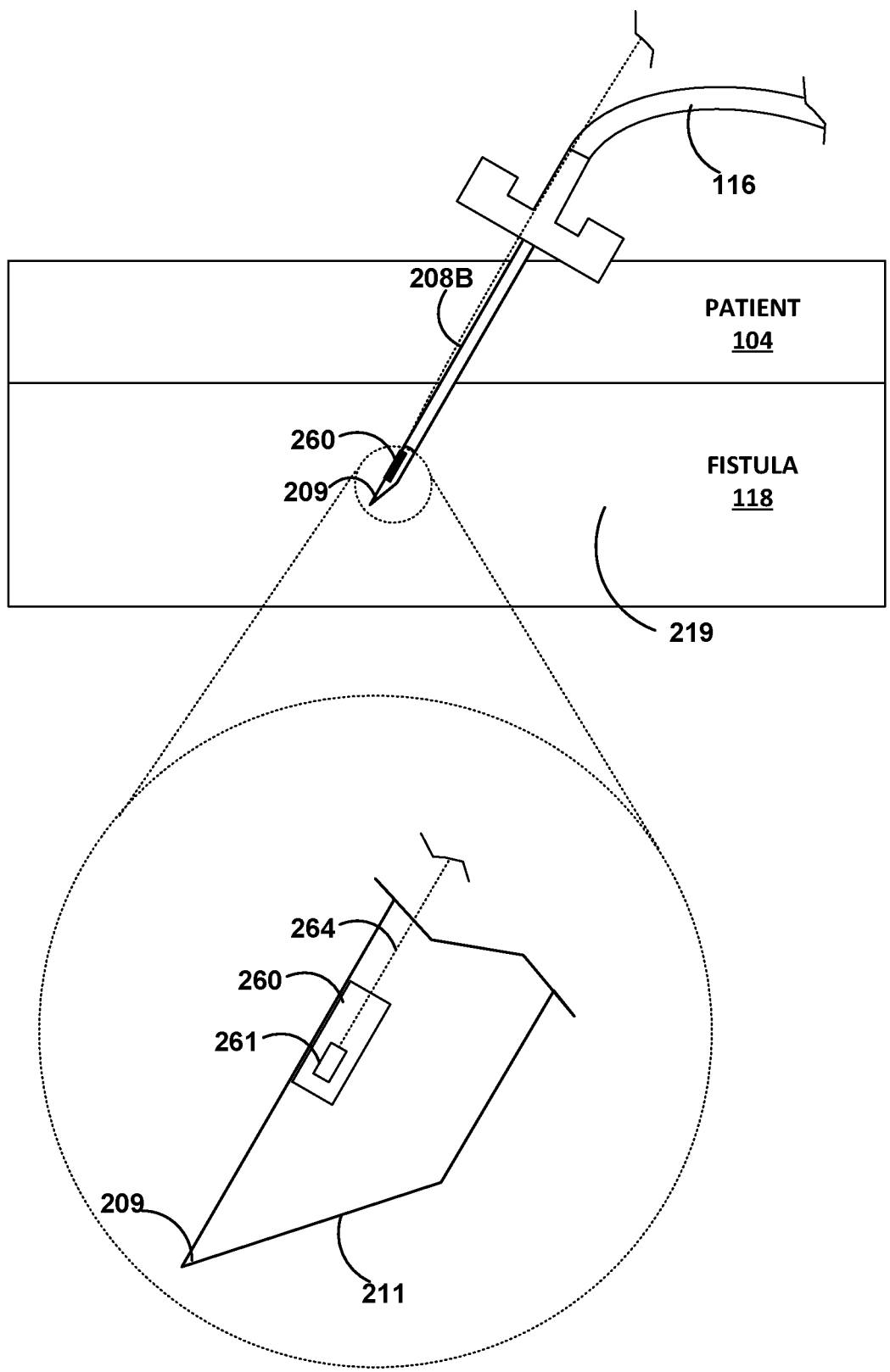
FIG. 2A-2C are conceptual diagrams illustrating an example venous needle including a pressure sensor.
Figure 2B:
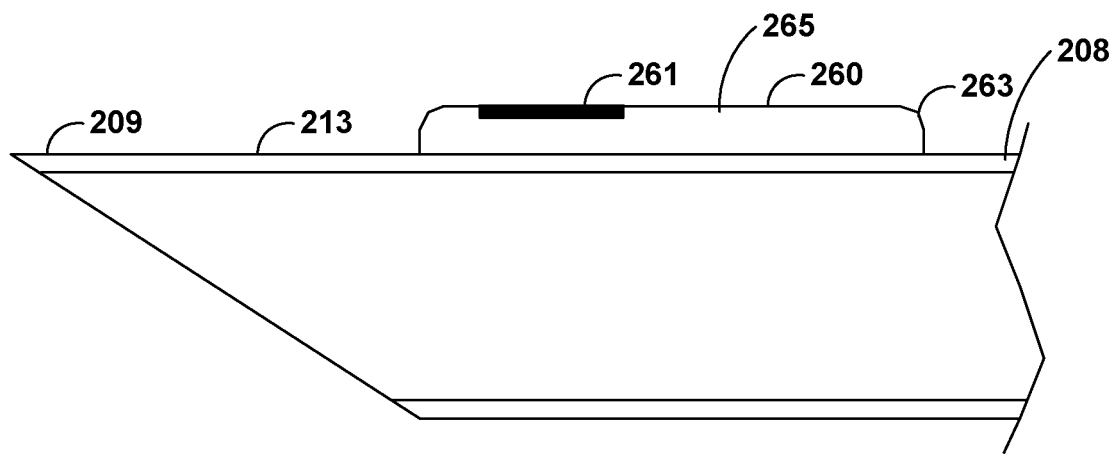
Figure 2C:
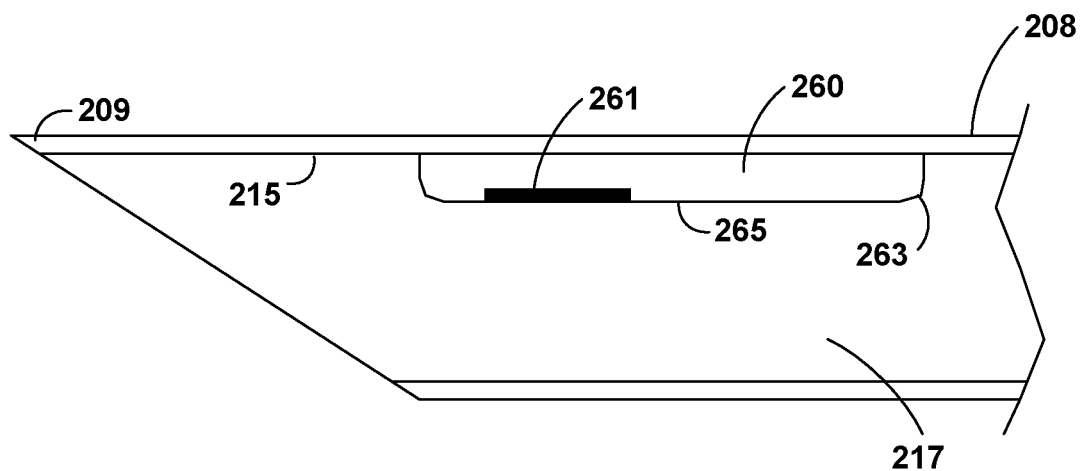

FIGS. 2A-2C are conceptual diagrams illustrating an example venous needle 208 including a pressure sensor 260. Venous needle 208 and pressure sensor 260 may be the same as or similar to venous needle 108B and pressure sensor 160, respectively, discussed above in reference to FIG. 1, except for the differences describe herein. In the view shown in FIG. 2A, venous needle 208 is fluidically coupled to venous line 116.

As illustrated in FIG. 2A, needle 208 includes distal tip 209 defining a sharp (e.g., incisive) tip or a blunt tip and a bevel 211, each configured to facilitate insertion of needle 208 into arteriovenous fistula 118. In examples in which pressure sensor 160 is on an elongate member such as a cannula or catheter, the elongate member may not include a tip configured to facilitate insertion of the elongate member into fistula 118, and a separate introduction tool may be used to introduce the elongate member into the vasculature of the patient.

In the example shown in FIG. 2A, pressure sensor 260 is located near a distal tip 209 of venous needle 208. For example, pressure sensor 260 may be any suitable distance from distal tip 209 such that at least a portion of pressure sensor 260, such as a pressure sensing surface 261 of pressure sensor 260, may be positioned within lumen 219 of arteriovenous fistula 118 when venous needle 208 is properly positioned in arteriovenous fistula 118 during hemodialysis. Pressure sensor 260, e.g., pressure sensing surface 261 is communicatively coupled to processing circuitry (e.g., processing circuitry 162) via connection 264. As discussed above, connection 264 may be a wired connection or a wireless connection.

Pressure sensor 260 may be attached to venous needle 208 by any suitable means. In some examples, a profile of pressure sensor 260 may be similar to at least a portion of venous needle 208 to facilitate attachment of pressure sensor 260 to a surface venous needle 208, as well as help pressure sensor 260 maintain a relatively low profile relative to surface of needle 208. For example, a curvature of pressure sensor 260 may match the curvature of a portion of venous needle 208. In this way, a low profile pressure sensor 260 may conform to the contour of a surface of venous needle 208 to ensure that the inner diameter of the inner lumen is not compromised and at the requisite dimensions to support the prescribed flow blood targets.

In some examples, pressure sensor 260 may be attached to venous needle 208 using an adhesive or via a welded connection. As another example, a first portion of pressure sensor 260 may be assembled into a small flattened section of the outer diameter of the needle shaft. The first portion of pressure sensor 260 may be attached to venous needle 208 using a MEMS layer on the inner or outer surface of the cannula or needle using laser, ultrasonic welding, or other non-destructive adhesion techniques. The first portion of pressure sensor 260 may be covered by a second portion of pressure sensor 260 that includes a flexible insulating membrane, such as, for example, a thin film of conductive material configured to act as a second electrode for an air gap capacitive type pressure sensor, or a thin film of a piezoelectric material configured to generate an electrical charge in response to physical shape change of the thin film. In some examples, a portion of venous needle 208 may be made out of the film of conductive material or thin film of piezoelectric material. In some examples, pressure sensor 260 may include a non-thrombogenic casing, e.g., as illustrated by smooth curved edges 263, and/or an antithrombogenic coating 265, such as, for example, a biocompatible material, silicones, or parylene.

In some examples, as illustrated in FIG. 2B, pressure sensor 260 may be attached to outer surface 213 of venous needle 208. In some examples, as illustrated in FIG. 2C, pressure sensor 260 may be positioned on inner surface 215 of venous needle 208. In either example, pressure sensor 260 may be positioned within the blood flow of arteriovenous fistula 118 when needle 208 is properly positioned within fistula 118 to return blood from dialysis device 102 and into fistula 118 during dialysis. For example, pressure sensor 260 may be with in a range from about 10 mm to about 20 mm (e.g., as close to 10 mm to 20 mm as permitted by manufacturing variances), such as about 10 mm to about 15 mm, from distal tip 209 of venous needle 208.

Inner surface 215 may defines a lumen 217 of venous needle 208. Lumen 217 is in fluidically coupled to lumen 219 of arteriovenous fistula 118 when venous needle 208 is properly positioned in arteriovenous fistula 118 during hemodialysis. In examples in which pressure sensor 260 is positioned on inner surface 215, pressure sensor 260 may be positioned further from distal tip 209 compared to a pressure sensor 260 positioned on outer surface 213. For example, pressure sensor 260 may be position any distance from distal tip 209 that enables pressure sensor 260 to sense a pulse pressure wave of an analog pressure signal, as discussed above.

In some examples, although not illustrated in FIGS. 2B and 2C, pressure sensor 260 may be at least partially embedded in venous needle 208. For example, pressure sensor 260 may be embedded in inner surface 215 of venous needle 208 such that pressure sensor 260 is substantially flush with inner surface 215 (e.g., flush or nearly flush within the limits of manufacturing tolerances) or at least to reduce the surface profile of pressure sensor 260 protruding from a surface of needle 208. Similarly, in some examples, pressure sensor 260 may be embedded in outer surface 213 such that pressure sensor 260 is substantially flush the outer surface 213. Embedding pressure sensor 260 in venous needle 208 may reduce the profile of pressure sensor 206 relative to the surface of venous needle 208 and, in some examples, may increase a contact surface area between pressure sensor 260 and a surface of venous needle 208 to improve adhesion or welding of pressure sensor 260 to venous needle 208. Reducing a profile of pressure sensor 260 may help reduce the possibility of thrombus formation due to the blood flow around pressure sensor 260.

Figure 3:
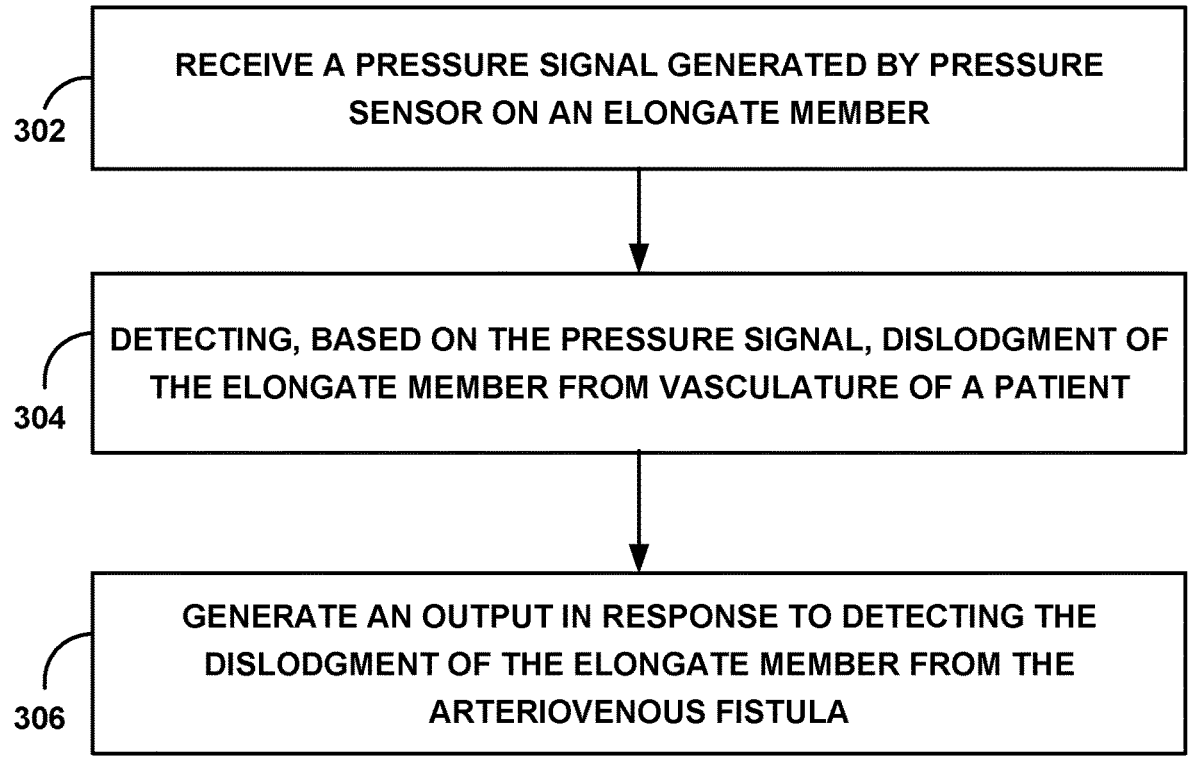
FIG. 3 is a flow diagram illustrating an example technique for determining of a patient state based on an output from a sensor of a PD system.

FIG. 3 is a flow diagram illustrating an example method of detecting dislodgment of an elongate member from vasculature of a patient. Although FIG. 3 is described with respect to processing circuitry 162 of dialysis system 100 (FIG. 1), in other examples, different processing circuitry, alone or in combination with processing circuitry 162, may perform any part of the technique of FIG. 3 to detect dislodgment of another elongate member from vasculature of a patient.

In accordance with the technique illustrated in FIG. 3, processing circuitry 162 receives a pressure signal generated by pressure sensor 160 on an elongate member (302). The elongate member may be configured to be introduced into arteriovenous fistula 118 of patient 104 and the pressure signal may be indicative of pressure adjacent elongate member. As discussed above, in some examples, the elongate member may include venous needle 108B fluidically coupled to dialysis unit 102 and configured to return the volume of dialyzed fluid to arteriovenous fistula 118.

Processing circuitry 162 detects, based on the pressure signal, dislodgment of the elongate member from vasculature of patient 14, such as from arteriovenous fistula 118 (304). In some examples, processing circuitry 162 detects dislodgment by at least determining a pressure adjacent the elongate member based on the pressure signal and comparing the pressure adjacent the elongate member with a threshold pressure stored by memory 168 of dialysis device 102 or a memory of another device. For example, processing circuitry 162 may detect the dislodgment (304) may include detecting the dislodgment of the elongate member, e.g., venous needle 108B, in response to determining the pressure adjacent the elongate member is greater than or equal to the threshold pressure. In some examples, the threshold pressure may be at least one of lower than a predetermined nominal fistula pressure and/or greater than an atmospheric pressure.

In examples in which the pressure signal includes an analog pressure signal, as discussed above, processing circuitry 162 can detect the elongate member dislodgment by at least determining the analog pressure signal does not include the natural pulse pressure wave component of the patient, thereby indicating the elongate member is no longer properly positioned within fistula 118. In some examples, processing circuitry 162 determines the analog pressure signal does not include the pulse pressure wave component by at least filtering out a dialysis pump pressure wave component from the analog pressure signal to generate a residual wave and determining that the residual wave does not include the pulse pressure wave component.

Processing circuitry 162 generates an output in response to detecting the dislodgment of the elongate member, e.g., venous needle 108B, from the arteriovenous fistula (306). In some examples, processing circuitry 162 generates the output (306) by at least controlling dialysis unit 102, e.g., to cause dialysis pump 124 of dialysis unit 102 to stop extracting fluid from arteriovenous fistula 118 via arterial needle 108B. In some examples, processing circuitry 162 generates the output (306) by at least generating and presenting, via user interface 170, a notification that instructs a user to reposition the elongate member (e.g., venous needle 108B) in arteriovenous fistula 118.

Figure 4:
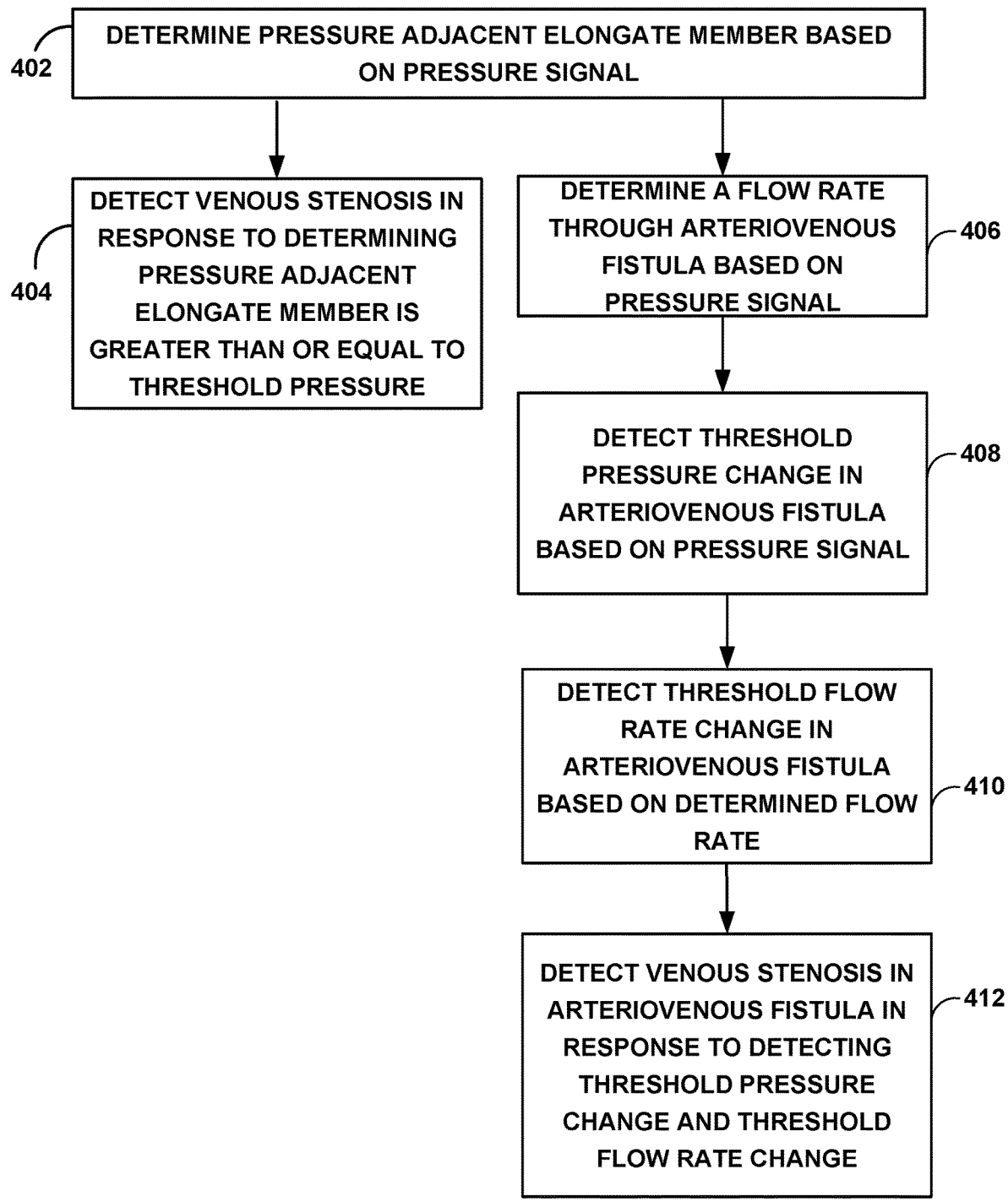
FIG. 4 is a flow diagram illustrating an example method of detecting venous stenosis in the vasculature of a patient.

In some examples, processing circuitry 162 is configured to detect a venous stenosis in arteriovenous fistula 118 based on a pressure signal generated by pressure sensor 160. FIG. 4 is a flow diagram illustrating an example method of detecting venous stenosis in the vasculature of a patient. Although FIG. 4 is described with respect to processing circuitry 162 of dialysis system 100 (FIG. 1), in other examples, different processing circuitry, alone or in combination with processing circuitry 162, may perform any part of the technique of FIG. 4 to detect venous stenosis in the vasculature of a patient.

In accordance with the technique illustrated in FIG. 4, processing circuitry 162 may determine a pressure adjacent the elongate member, e.g., venous needle 108B, based on a pressure signal generated by pressure sensor 160 (e.g., alone or in combination with pressure sensing circuitry 166) (402). Processing circuitry 162 may detect the venous stenosis in response to determining the pressure adjacent the elongate member is greater than or equal to a threshold pressure (404).

In some examples, as discussed above, to detect the venous stenosis, processing circuitry 162 may determine a flow rate through arteriovenous fistula 118 based on the pressure signal (406). Processing circuitry 162 may detect a threshold pressure change in arteriovenous fistula 118 based on the pressure signal (408). Processing circuitry 162 may detect a threshold flow rate change in arteriovenous fistula 118 based on the determined flow rate (410). Processing circuitry 162 may detect the venous stenosis in arteriovenous fistula 118 in response to detecting the threshold pressure change and the threshold flow rate change (412). In some examples, in response to detecting the venous stenosis, processing circuitry 162 modifies an operation of dialysis unit 102, which is configured to deliver fluid to the patient via the elongate member.

The following clauses illustrate example subject matter disclosure herein.

Clause 1. A system comprising: an elongate member configured to be introduced into vasculature of a patient, wherein the elongate member comprises a pressure sensor configured to generate a pressure signal indicative of pressure adjacent the elongate member; and processing circuitry configured to: receive the pressure signal from the pressure sensor, detect, based on the pressure signal, dislodgment of the elongate member from the vasculature, and generate an output in response to detecting the dislodgment of the elongate member from the vasculature.

Clause 2. The system of clause 1, wherein the elongate member comprises at least one of a needle, a catheter, or a cannula.

Clause 3. The system of clause 1 or clause 2, wherein the elongate member comprises a venous needle, the system further comprising: an arterial needle configured to be introduced into the vasculature; and a dialysis unit fluidically coupled to the venous needle and the arterial needle.

Clause 4. The system of clause 3, wherein the dialysis unit is configured to dialyze a volume of fluid extracted from the vasculature through the arterial needle and return a volume of dialyzed fluid to the vasculature through the venous needle.

Clause 5. The system of clause 3, wherein the processing circuitry is configured to generate the output by at least controlling the dialysis unit based on the detection of the dislodgment of the venous needle from the vasculature.

Clause 6. The system of clause 5, wherein the processing circuitry is configured to control the dialysis unit by at least causing a dialysis pump of the dialysis unit to stop extracting fluid from the vasculature.

Clause 7. The system of any of clauses 1-6, further comprising a user interface, wherein the processing circuitry is configured to generate the output by at least presenting a notification via the user interface that instructs a user to reposition the elongate member in the vasculature.

Clause 8. The system of any of clauses 1-7, wherein the processing circuitry is configured to detect the dislodgment of the elongate member by at least: determining the pressure adjacent the elongate member based on the pressure signal; and comparing the pressure adjacent the elongate member with a threshold pressure.

Clause 9. The system of clause 8, wherein the processing circuitry is configured to detect the dislodgment of the elongate member in response to determining the pressure adjacent the elongate member is less than or equal to the threshold pressure.

Clause 10. The system of clause 8, wherein the threshold pressure is at least one of lower than a predetermined nominal pressure or greater than an atmospheric pressure.

Clause 11. The system of any of clauses 1-10, wherein the pressure signal comprises an analog pressure signal, and wherein the processing circuitry is configured to detect the dislodgment of the elongate member by at least: determining the analog pressure signal does not include a pulse pressure wave component, the pulse pressure wave being indicative of a pulse pressure of the patient; and detecting the dislodgment of the elongate member in response to determining the analog pressure signal does not include the pulse pressure wave component.

Clause 12. The system of clause 11, wherein the processing circuitry is configured to determine the analog pressure signal does not include the pulse pressure wave component by at least: detecting a dialysis pump pressure wave component in the analog pressure signal, generating a residual wave by at least filtering the dialysis pump pressure wave component from the analog pressure signal, and determining the residual wave does not include the pulse pressure wave component.

Clause 13. The system of any of clauses 1-12, wherein the elongate member comprises an inner surface defining a lumen, wherein the pressure sensor is positioned along the inner surface.

Clause 14. The system of any of clauses 1-12, wherein the elongate member comprises an outer surface, wherein the pressure sensor is positioned along the outer surface.

Clause 15. The system of any of clauses 1-12, wherein the elongate member defines an inner surface and an outer surface, the pressure sensor being at least partially embedded in at least one of the inner surface or the outer surface.

Clause 16. The system of any of clauses 1-15, wherein the pressure sensor comprises a micro-electro-mechanical systems (MEMS) pressure sensor.

Clause 17. The system of any of clauses 1-16, wherein the processing circuitry is configured to detect a venous stenosis in the vasculature based on the pressure signal.

Clause 18. The system of clause 17, wherein the processing circuitry is configured to detect the venous stenosis in response to determining a pressure adjacent the elongate member based on the pressure signal and determining the pressure is greater than or equal to a threshold pressure.

Clause 19. The system of clause 18, further comprising a dialysis unit configured to deliver fluid to the patient via the elongate member, wherein the processing circuitry is configured to modify an operation of the dialysis unit in response to detecting the venous stenosis.

Clause 20. The system of clause 17, wherein the processing circuitry is configured to detect the venous stenosis by at least: determining a flow rate through the vasculature based on the pressure signal; detecting a threshold pressure change in the vasculature based on the pressure signal; detecting a threshold flow rate change in the vasculature based on the determined flow rate; and detecting the venous stenosis in the vasculature in response to detecting the threshold pressure change and the threshold flow rate change.

Clause 21. The system of clause 20, further comprising a dialysis unit configured to deliver fluid to the patient via the elongate member, wherein the processing circuitry is configured to modify an operation of the dialysis unit in response to detecting the venous stenosis.

Clause 22. The system of any of clauses 1-21, further comprising a reference pressure sensor configured to generate a reference pressure signal indicative of a reference pressure external to the vasculature, wherein the processing circuitry is configured to detect the dislodgment of the elongate member based on the pressure signal and the reference pressure signal.

Clause 23. The system of clause 22, wherein the processing circuitry is configured to detect the dislodgment of the elongate member based on the pressure signal and the reference pressure signal by at least: determining, based on the pressure signal and the reference pressure signal, a differential pressure; and comparing the differential pressure with a threshold pressure.

Clause 24. The system of clause 22, wherein the processing circuitry is configured to detect the dislodgment of the elongate member based on the pressure signal and the reference pressure signal by at least: determining, based on the pressure signal and the reference pressure signal, a differential pressure; determining a rate of change of the differential pressure over time; comparing the rate of change of the differential pressure with a threshold rate of change.

Clause 25. The system of any of clauses 1-24, wherein the vasculature of the patient comprises an arteriovenous fistula or an arteriovenous graft.

Clause 26. A method comprising: receiving, by processing circuitry, a pressure signal generated by a pressure sensor on an elongate member configured to be introduced into vasculature of a patient, the pressure signal being indicative of pressure adjacent the elongate member; detecting, by the processing circuitry and based on the pressure signal, dislodgment of the elongate member from the vasculature; and generating, by the processing circuitry, an output in response to detecting the dislodgment of the elongate member from the vasculature.

Clause 27. The method of clause 26, wherein the elongate member comprises a venous needle fluidically coupled to a dialysis unit, the dialysis unit being configured to dialyze a volume of fluid extracted from the vasculature through an arterial needle and return the volume of dialyzed fluid to the vasculature through the venous needle.

Clause 28. The method of clause 27, wherein generating the output comprises controlling the dialysis unit based on the detection of the dislodgment of the venous needle.

Clause 29. The method of clause 28, wherein controlling the dialysis unit comprises causing a dialysis pump of the dialysis unit to stop extracting fluid from the vasculature via the arterial needle.

Clause 30. The method of any of clauses 26-29, wherein generating the output comprises presenting, via a user interface, a notification that instructs a user to reposition the elongate member in the vasculature.

Clause 31. The method of any of clauses 26-30, wherein detecting the dislodgment of the elongate member comprises: determining a pressure adjacent the elongate member based on the pressure signal; and comparing the pressure adjacent the elongate member with a threshold pressure.

Clause 32. The method of any of clauses 26-31, wherein detecting the dislodgment of the elongate member comprises detecting the dislodgment of the elongate member in response to determining the pressure adjacent the elongate member is greater than or equal to the threshold pressure.

Clause 33. The method of clause 32, wherein the threshold pressure is at least one of lower than a predetermined nominal pressure or greater than an atmospheric pressure.

Clause 34. The method of any of clauses 26-33, wherein the pressure signal comprises an analog pressure signal, and wherein detecting the dislodgment of the elongate member comprises: determining the analog pressure signal does not include a pulse pressure wave component, the pulse pressure wave being indicative of a pulse pressure of the patient; and detecting the dislodgment of the elongate member in response to determining the analog pressure signal does not include the pulse pressure wave component.

Clause 35. The method of clause 34, wherein determining the analog pressure signal does not include the pulse pressure wave component comprises: detecting a dialysis pump pressure wave component in the analog pressure signal, generating a residual wave by at least filtering the dialysis pump pressure wave component from the analog pressure signal, and determining the residual wave does not include the pulse pressure wave component.

Clause 36. The method of any of clauses 26-35, wherein the pressure sensor comprises a micro-electro-mechanical systems (MEMS) pressure sensor.

Clause 37. The method of any of clauses 26-36, further comprising detecting a venous stenosis in the vasculature based on the pressure signal.

Clause 38. The method of clause 37, wherein detecting the venous stenosis comprises:
determining a pressure adjacent the elongate member based on the pressure signal; and
detecting the venous stenosis in response to determining the pressure adjacent the elongate member is greater than or equal to a threshold pressure.

Clause 39. The method of clause 37, wherein detecting the venous stenosis comprises: determining a flow rate through the vasculature based on the pressure signal; detecting a threshold pressure change in the vasculature based on the pressure signal; detecting a threshold flow rate change in the vasculature based on the determined flow rate; and detecting the venous stenosis in the vasculature in response to detecting the threshold pressure change and the threshold flow rate change.

Clause 40. The method of clause 39, further comprising modifying an operation of a dialysis unit in response to detecting the venous stenosis, the dialysis unit being configured to deliver fluid to the patient via the elongate member.

Clause 41. The method of any of clauses 26-40, wherein receiving the pressure signal generated by the pressure sensor comprises receiving the pressure signal generated by the pressure sensor on the elongate member configured to be introduced into an arteriovenous fistula or an arteriovenous graft of the patient.

Clause 42. The method of any of clauses 26-41, further comprising receiving, by the processing circuitry, a reference pressure signal indicative of a reference pressure external to the vasculature, wherein detecting dislodgment of the elongate member from the vasculature comprises detecting the dislodgment of the elongate member based on the pressure signal and the reference pressure signal.

Clause 43. The system method of clause 42, wherein detecting the dislodgment of the elongate member based on the pressure signal and the reference pressure signal comprises: determining, based on the pressure signal and the reference pressure signal, a differential pressure; and comparing the differential pressure with a threshold pressure.

Clause 44. The system method of clause 42, wherein detecting the dislodgment of the elongate member based on the pressure signal and the reference pressure signal comprises: determining, based on the pressure signal and the reference pressure signal, a differential pressure; determining a rate of change of the differential pressure over time; and comparing the rate of change of the differential pressure with a threshold rate of change.

Clause 45. A system comprising: means for generating a pressure signal indicative of pressure adjacent an elongate member configured to be introduced into vasculature of a patient; and means for detecting dislodgment of the elongate member from the vasculature based on the pressure signal; and means for generating an output in response to detecting the dislodgment of the needle from the vasculature.

Clause 46. The system of clause 45, wherein the means for detecting dislodgment of the elongate member detects the dislodgment of the elongate member in response to determining a pressure adjacent the elongate member based on the pressure signal and determining the pressure is greater than or equal to a threshold pressure.

Clause 47. The system of clause 45 or clause 46, wherein the pressure signal comprises an analog pressure signal, and wherein the means for detecting dislodgment of the elongate member comprises: means for determining the analog pressure signal does not include a pulse pressure wave component, the pulse pressure wave being indicative of a pulse pressure of the patient; and means for detecting the dislodgment of the elongate member in response to determining the analog pressure signal does not include the pulse pressure wave component.

Clause 48. The system of any of clauses 45-47, wherein the vasculature includes an arteriovenous fistula or an arteriovenous graft.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to hemodialysis system 100, processing circuitry 162, memory 168, user interface 170, pressure sensing circuitry 166, control circuitry 126, and various constituent components thereof, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between hemodialysis system 100, processing circuitry 162, memory 168, user interface 170, pressure sensing circuitry 166, and/or control circuitry 126. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, hemodialysis system 100, processing circuitry 162, memory 168, user interface 170, pressure sensing circuitry 166, and control circuitry 126 may be programmed with various forms of software. The one or more processors may be implemented at least in part as, or include, one or more executable applications, application modules, libraries, classes, methods, objects, routines, subroutines, firmware, and/or embedded code, for example.

In examples in which processing circuitry 162 is described herein as determining that a value is less than or equal to another value, this description may also include processing circuitry 162 determining that a value is only less than the other value. Similarly, in examples in which processing circuitry 162 is described herein as determining that a value is less than another value, this description may also include processing circuitry 162 determining that a value is less than or equal to the other value. The same properties may also apply to the terms "greater than" and "greater than or equal to."

Various examples have been described. These and other examples are within the scope of the following claims.

What is claimed is:

1. A system comprising:
an elongate member configured to be introduced into vasculature of a patient, wherein the elongate member comprises a pressure sensor configured to generate a pressure signal indicative of pressure adjacent the elongate member; and
processing circuitry configured to:
receive the pressure signal from the pressure sensor, detect, based on the pressure signal, dislodgment of the elongate member from the vasculature, and
generate an output in response to detecting the dislodgment of the elongate member from the vasculature,
wherein the processing circuitry is configured to detect the dislodgment of the elongate member by at least:
  determining the pressure adjacent the elongate member based on the pressure signal; and
  comparing the pressure adjacent the elongate member with a threshold pressure value.

2. The system of claim 1, wherein the elongate member comprises at least one of a needle, a catheter, or a cannula.

3. The system of claim 1, wherein the elongate member comprises a venous needle, the system further comprising:
  an arterial needle configured to be introduced into the vasculature; and
  a dialysis unit fluidically coupled to the venous needle and the arterial needle.

4. The system of claim 3, wherein the dialysis unit is configured to dialyze a volume of fluid extracted from the vasculature through the arterial needle and return a volume of dialyzed fluid to the vasculature through the venous needle.

5. The system of claim 3, wherein the processing circuitry is configured to generate the output by at least controlling the dialysis unit based on the detection of the dislodgment of the venous needle from the vasculature.

6. The system of claim 5, wherein the processing circuitry is configured to control the dialysis unit by at least causing a dialysis pump of the dialysis unit to stop extracting fluid from the vasculature.

7. The system of claim 1, further comprising a user interface, wherein the processing circuitry is configured to generate the output by at least presenting a notification via the user interface that instructs a user to reposition the elongate member in the vasculature.

8. The system of claim 1, wherein the processing circuitry is configured to detect the dislodgment of the elongate member in response to determining the pressure adjacent the elongate member is less than or equal to the threshold pressure value.

9. The system of claim 1, wherein the threshold pressure value is at least one of lower than a predetermined nominal pressure or greater than an atmospheric pressure value.

10. A system comprising:
  an elongate member configured to be introduced into vasculature of a patient, wherein the elongate member comprises a pressure sensor configured to generate a pressure signal indicative of pressure adjacent the elongate member; and
  processing circuitry configured to:
    receive the pressure signal from the pressure sensor,
    detect, based on the pressure signal, dislodgment of the elongate member from the vasculature, and
    generate an output in response to detecting the dislodgment of the elongate member from the vasculature,
    wherein the pressure signal comprises an analog pressure signal, and wherein the processing circuitry is configured to detect the dislodgment of the elongate member by at least:
      determining the analog pressure signal does not include a pulse pressure wave component, the pulse pressure wave being indicative of a pulse pressure of the patient, wherein to determine the analog pressure signal does not include the pulse wave component, the processing circuitry is configured to:
        detect a dialysis pump pressure wave component in the analog pressure signal,
        generate a residual wave by at least filtering the dialysis pump pressure wave component from the analog pressure signal, and
        determine the residual wave does not include the pulse pressure wave component; and
      detecting the dislodgment of the elongate member in response to determining the analog pressure signal does not include the pulse pressure wave component.

11. The system of claim 1, wherein the elongate member comprises an inner surface defining a lumen, wherein the pressure sensor is positioned along the inner surface.

12. The system of claim 1, wherein the elongate member comprises an outer surface, wherein the pressure sensor is positioned along the outer surface.

13. The system of claim 1, wherein the elongate member defines an inner surface and an outer surface, the pressure sensor being at least partially embedded in at least one of the inner surface or the outer surface.

14. The system of claim 1, wherein the pressure sensor comprises a micro-electro-mechanical systems (MEMS) pressure sensor.

15. The system of claim 1, wherein the processing circuitry is configured to detect a venous stenosis in the vasculature based on the pressure signal.

16. The system of claim 15, wherein the threshold pressure value comprises a first threshold pressure value, and wherein the processing circuitry is configured to detect the venous stenosis in response to determining the pressure adjacent the elongate member is greater than or equal to a second threshold pressure value.

17. The system of claim 16, further comprising a dialysis unit configured to deliver fluid to the patient via the elongate member, wherein the processing circuitry is configured to modify an operation of the dialysis unit in response to detecting the venous stenosis.

18. The system of claim 15, wherein the processing circuitry is configured to detect the venous stenosis by at least:
  determining a flow rate through the vasculature based on the pressure signal;
  detecting a threshold pressure change in the vasculature based on the pressure signal;
  detecting a threshold flow rate change in the vasculature based on the determined flow rate; and
  detecting the venous stenosis in the vasculature in response to detecting the threshold pressure change and the threshold flow rate change.

19. The system of claim 18, further comprising a dialysis unit configured to deliver fluid to the patient via the elongate member, wherein the processing circuitry is configured to modify an operation of the dialysis unit in response to detecting the venous stenosis.

20. A system comprising:
  an elongate member configured to be introduced into vasculature of a patient, wherein the elongate member comprises a pressure sensor configured to generate a pressure signal indicative of pressure adjacent the elongate member;
  a reference pressure sensor configured to generate a reference pressure signal indicative of a reference pressure external to the vasculature; and
  processing circuitry configured to:
    receive the pressure signal from the pressure sensor, detect, based on the pressure signal and the reference pressure signal, dislodgment of the elongate member from the vasculature, and generate an output in response to detecting the dislodgment of the elongate member from the vasculature.

21. The system of claim 20, wherein the processing circuitry is configured to detect the dislodgment of the elongate member based on the pressure signal and the reference pressure signal by at least:

determining, based on the pressure signal and the reference pressure signal, a differential pressure; and comparing the differential pressure with a threshold pressure.

22. The system of claim 20, wherein the processing circuitry is configured to detect the dislodgment of the elongate member based on the pressure signal and the reference pressure signal by at least:

determining, based on the pressure signal and the reference pressure signal, a differential pressure;

determining a rate of change of the differential pressure over time; and comparing the rate of change of the differential pressure with a threshold rate of change.

23. The system of claim 1, wherein the vasculature of the patient comprises an arteriovenous fistula or an arteriovenous graft.

24. The system of claim 10, wherein the processing circuitry is configured to detect a venous stenosis in the vasculature based on the pressure signal.

25. The system of claim 24, wherein the processing circuitry is configured to detect the venous stenosis by at least:

determining a flow rate through the vasculature based on the pressure signal;

detecting a threshold pressure change in the vasculature based on the pressure signal;

detecting a threshold flow rate change in the vasculature based on the determined flow rate; and detecting the venous stenosis in the vasculature in response to detecting the threshold pressure change and the threshold flow rate change.

* * * * *